US 9,173,549 B2

(12) United States Patent
Naito

(10) Patent No.: US 9,173,549 B2
(45) Date of Patent: Nov. 3, 2015

(54) BIOLOGICAL INTRODUCTION APPARATUS AND ENDOSCOPE HAVING BIOLOGICAL INTRODUCTION APPARATUS

(71) Applicant: OLYMPUS MEDICAL SYSTEMS CORP., Tokyo (JP)

(72) Inventor: Kimihiko Naito, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/933,240

(22) Filed: Jul. 2, 2013

(65) Prior Publication Data

US 2014/0012084 A1 Jan. 9, 2014

Related U.S. Application Data

(63) Continuation of application No. PCT/JP2012/077894, filed on Oct. 29, 2012.

(30) Foreign Application Priority Data

Mar. 29, 2012 (JP) .................................. 2012-076176

(51) Int. Cl.
*A61B 1/04* (2006.01)
*A61B 1/00* (2006.01)

(52) U.S. Cl.
CPC ........... *A61B 1/0016* (2013.01); *A61B 1/00071* (2013.01)

(58) Field of Classification Search
USPC .......................... 600/114, 137, 104, 127, 129; 604/103.08, 528, 533, 544; 348/45; 356/241.1–241.6
See application file for complete search history.

(56) References Cited

U.S. PATENT DOCUMENTS

| | | | |
|---|---|---|---|
| 6,315,714 B1 * | 11/2001 | Akiba | 600/114 |
| 8,277,374 B2 * | 10/2012 | Tsumaru et al. | 600/115 |
| 8,317,678 B2 * | 11/2012 | Frassica et al. | 600/101 |
| 2005/0272976 A1 * | 12/2005 | Tanaka et al. | 600/114 |
| 2006/0270901 A1 | 11/2006 | Bern et al. | |
| 2007/0167684 A1 * | 7/2007 | Toyama | 600/128 |
| 2009/0012359 A1 * | 1/2009 | Tanaka et al. | 600/114 |

(Continued)

FOREIGN PATENT DOCUMENTS

| | | |
|---|---|---|
| JP | 2006-230620 A | 9/2006 |
| JP | 2009-501555 A | 1/2009 |

(Continued)

OTHER PUBLICATIONS

International Search Report from corresponding International Application No. PCT/JP2012/077894, dated Nov. 27, 2012.

(Continued)

*Primary Examiner* — Anhtuan T Nguyen
*Assistant Examiner* — Timothy J Neal
(74) *Attorney, Agent, or Firm* — Scully, Scott, Murphy & Presser, P.C.

(57) ABSTRACT

The biological introduction apparatus includes a drive force generation and input mechanism, a drive force transmission mechanism, a helical rotation member, a holding member and a positioning mechanism. The positioning mechanism positions a proximal end portion of a main body portion which is arranged in the helical rotation member to an intermediate portion arranged between a distal end portion of an insertion unit and a proximal end portion of the insertion unit.

15 Claims, 8 Drawing Sheets

(56) References Cited

U.S. PATENT DOCUMENTS

| | | | |
|---|---|---|---|
| 2009/0023994 A1* | 1/2009 | Kura et al. ................... | 600/114 |
| 2009/0209812 A1* | 8/2009 | Omoto ......................... | 600/110 |
| 2011/0319713 A1 | 12/2011 | Frassica et al. | |

FOREIGN PATENT DOCUMENTS

| | | |
|---|---|---|
| JP | 2009-165640 A | 7/2009 |
| JP | 2009-254554 A | 11/2009 |
| JP | 2010-527651 A | 8/2010 |
| JP | 2011-520563 A | 7/2011 |
| JP | 2011-161138 A | 8/2011 |

OTHER PUBLICATIONS

English abstract only of WO 2008/144033 A2 dated Nov. 27, 2008.
English abstract only of WO 2009/143077 A1 dated Jul. 21, 2011.
International Preliminary Report on Patentability together with the Written Opinion dated Oct. 9, 2014 received in related International Application No. PCT/JP2012/077894.
Chinese Office Action dated Feb. 11, 2015 received from Application No. 201280022446.3, together with an English-language translation.

* cited by examiner

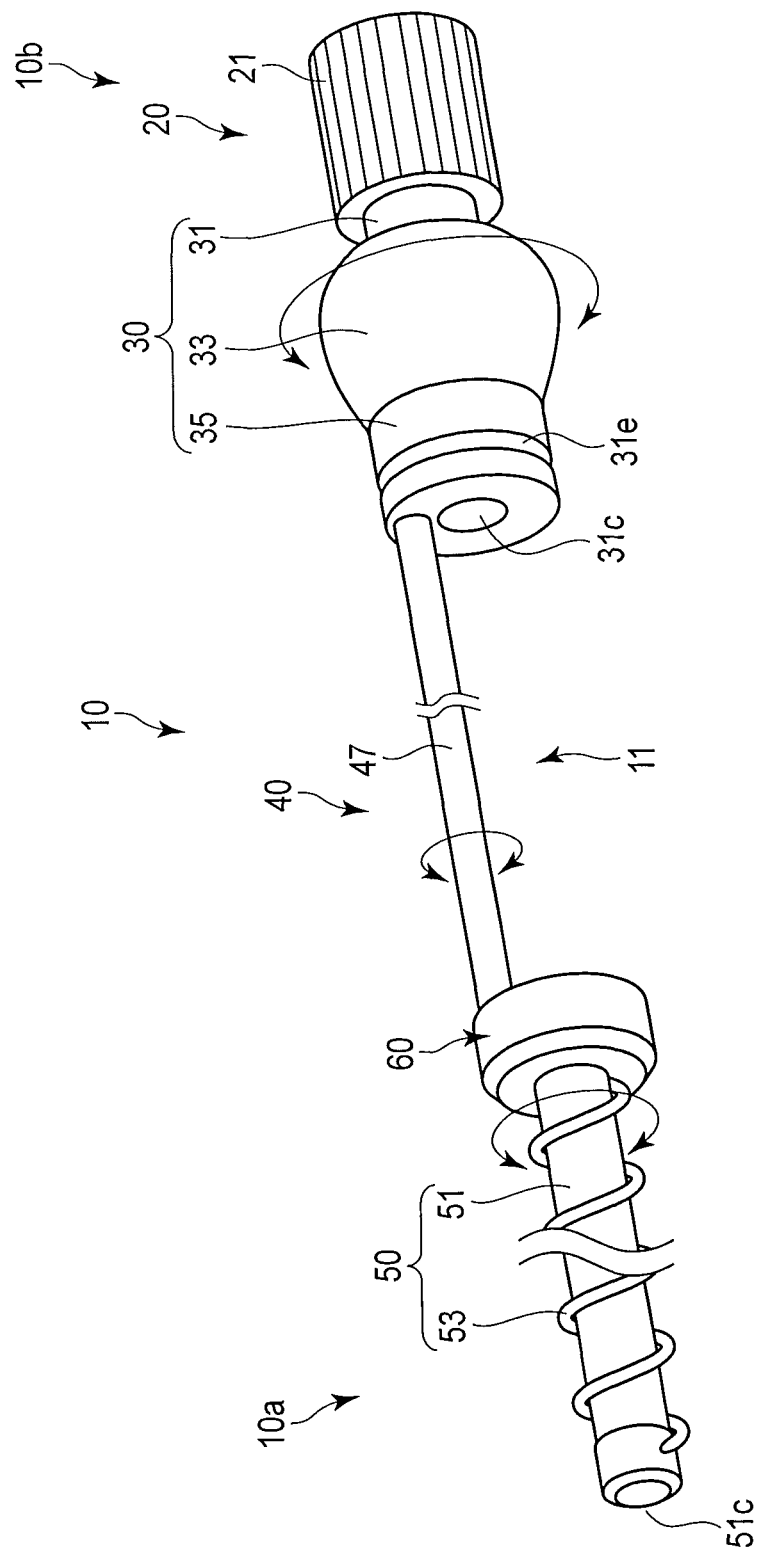
F I G. 2

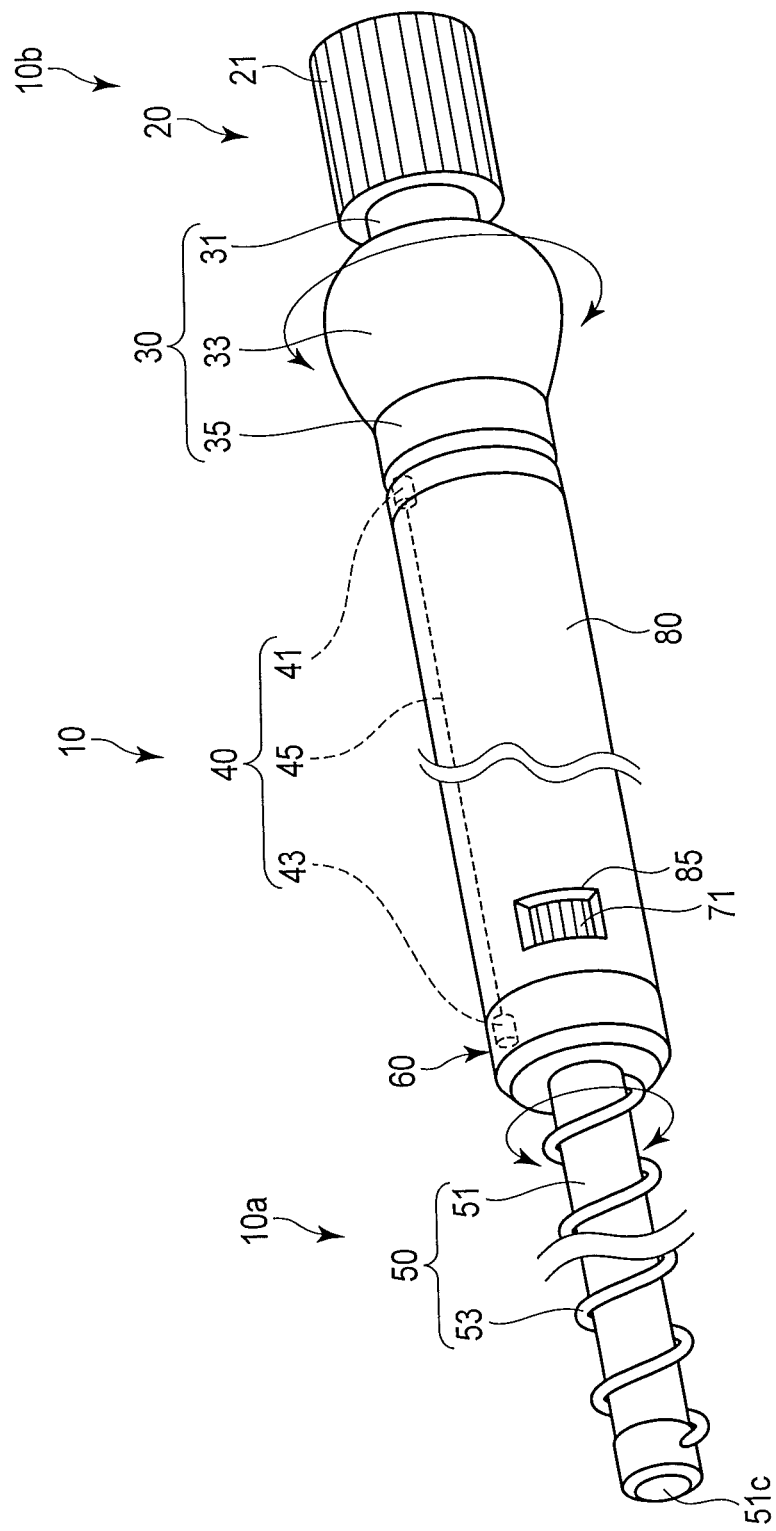
F I G. 4A

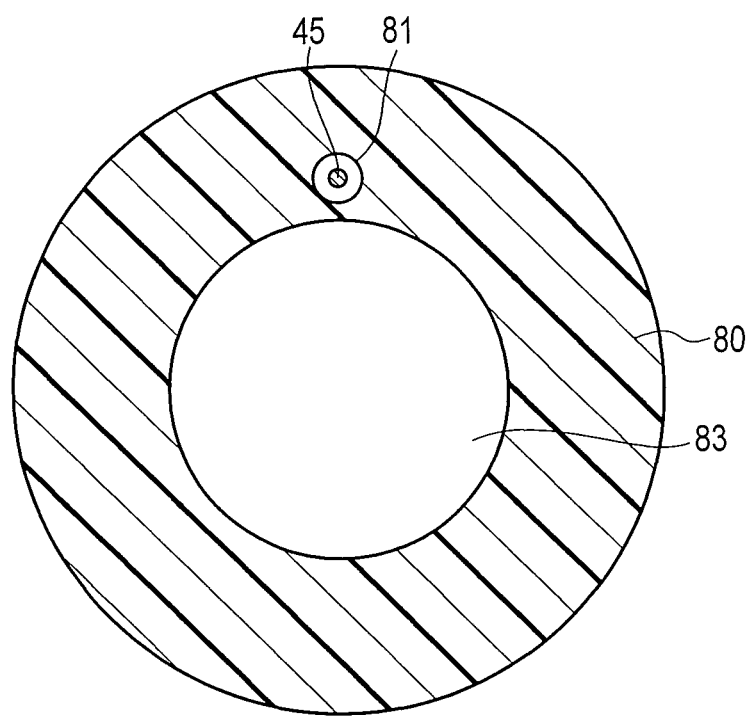
F I G. 4C

BIOLOGICAL INTRODUCTION APPARATUS AND ENDOSCOPE HAVING BIOLOGICAL INTRODUCTION APPARATUS

CROSS-REFERENCE TO RELATED APPLICATIONS

This application is a Continuation Application of PCT Application No. PCT/JP2012/077894, filed Oct. 29, 2012, and based upon and claiming the benefit of priority from prior Japanese Patent Application No. 2012-076176, filed Mar. 29, 2012, the entire contents of all of which are incorporated herein by reference.

BACKGROUND OF THE INVENTION

1. Field of the Invention

The present invention relates to a biological introduction apparatus that introduces an insertion unit of an endoscope into a living body and an endoscope having this biological introduction apparatus.

2. Description of the Related Art

For example, Jpn. Pat. Appln. KOKAI Publication No. 2011-161138 discloses an endoscope insertion auxiliary tool arranged at a distal end portion of an insertion unit. This endoscope insertion auxiliary tool has a bag-shaped traveling unit and a support unit that is arranged in the traveling unit and supports the traveling unit. The support unit has a worm gear and a peripheral tooth portion that is arranged at a proximal end portion of the worm gear and arranged over an entire periphery along a circumferential direction of the proximal end portion. The peripheral tooth portion meshes with a pinion arranged at a distal end portion of a torque wire. At this time, the peripheral tooth portion and the pinion are arranged in the traveling unit. A proximal end portion of the torque wire is connected with a drive source.

When the drive source drives, the torque wire rotates, and the worm gear rotates through the pinion and the peripheral tooth portion in accordance with this rotation. As a result, the traveling unit circulates so that the outer side of the traveling unit travels in a counter-inserting direction and the inner side of the traveling unit travels in an inserting direction, for example. When the traveling unit circulates, the insertion unit obtains propulsive force. As a result, for example, forward movement of the insertion unit is aided by this propulsive force.

Further, for example, Jpn. Pat. Appln. KOKAI Publication No. 2010-527651 discloses a catheter. This catheter has a corrugated pipe into which an endoscope is inserted and a helical screw arranged at a distal end portion of the corrugated pipe. Furthermore, the catheter has a handle that is arranged apart from the helical screw, arranged at a proximal end portion of the corrugated pipe, and rotates the helical screw through the corrugated pipe and a fixing portion that is arranged to be closer to a proximal end portion of the corrugated pipe than the handle and fixes an endoscope.

The corrugated pipe is arranged over the entire circumference in the circumferential direction of the catheter. The helical screw is arranged on an outer peripheral surface of the corrugated pipe, and it is also helically arranged around a longitudinal axis of the corrugated pipe. When the handle rotates, the corrugated pipe rotates, and the helical screw rotates in accordance with the rotation of the corrugated pipe. When the rotating helical screw engages with an inner wall of a lumen, the corrugated pipe obtains the propulsive force. As a result, for example, forward movement of the corrugated pipe is aided by this propulsive force.

BRIEF SUMMARY OF THE INVENTION

According to one aspect of a biological introduction apparatus according to the present invention, there is provided a biological introduction apparatus which is introduced into a living body in a state that an insertion unit of an endoscope having a longitudinal axis is inserted therethrough, and has a distal end portion and a proximal end portion, comprising: a drive force generation and input mechanism which has an insertion hole through which the insertion unit is inserted, is arranged on the proximal end portion side, generates drive force by rotating in a periaxial direction of the longitudinal axis, and inputs the drive force; a drive force transmission mechanism which is arranged on the distal end portion side than the drive force generation and input mechanism, arranged on an outer side than the insertion unit inserted through the insertion hole in a radial direction of the insertion unit, and arranged on part of a circumference of the biological introduction apparatus in a circumferential direction thereof, the drive force transmission mechanism having an elongated shaft member which rotates in the periaxial direction by the drive force input by the drive force generation and input mechanism to transmit the drive force; a helical rotation member which has: a cylindrical main body portion which has flexibility, through which the insertion unit is inserted, and rotates in the periaxial direction of the longitudinal axis by the drive force transmitted by the shaft member; and a fin portion which is arranged on an outer peripheral surface of the main body portion and also helically arranged in the periaxial direction of the longitudinal axis, the helical rotation member being arranged on the distal end portion side; a holding member which has an insertion hole through which a proximal end portion of the main body portion is inserted, is arranged on the proximal end portion side of the biological introduction apparatus than the fin portion in the longitudinal axis direction, and holds the proximal end portion side of the main body portion in such a manner that the proximal end portion side of the main body portion is coupled with a distal end portion of the shaft member with the proximal end portion of the main body portion being inserted through the insertion hole, the drive force is transmitted from the distal end portion of the shaft member to the proximal end portion side of the main body portion, and the main body portion rotates in the periaxial direction of the longitudinal axis by the drive force; and a positioning mechanism which positions the proximal end portion of the main body portion to an intermediate portion arranged between the distal end portion of the insertion unit and the proximal end portion of the insertion unit in such a manner that the helical rotation member is positioned to the insertion unit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general descrip

FIG. 2 is a perspective view of the biological introduction apparatus shown in FIG. 1;

FIG. 4A is a perspective view of a biological introduction apparatus according to a second embodiment;

FIG. 4C is a schematic cross-sectional view taken along line 4C-4C depicted in FIG. 4B.

DETAILED DESCRIPTION OF THE INVENTION

Embodiments according to the present invention will now be described hereinafter with reference to the drawings.

First Embodiment

Configuration

A first embodiment will now be described with reference to FIG. 1, FIG. 2, FIG. 3A, FIG. 3B, FIG. 3C, and FIG. 3D. It is to be noted that some of members are omitted in some of the drawings to clarify the drawings, for example, a holding member 60 is omitted in FIG. 3C. Further, in the following description, a longitudinal axis means a longitudinal axis of an insertion unit 101 of an endoscope 100. A longitudinal axis direction means, for example, a longitudinal axis direction of the insertion unit 101. A radial direction means a radial direction of the insertion unit 101.

[Configuration of Endoscope 100]

Figure 1:
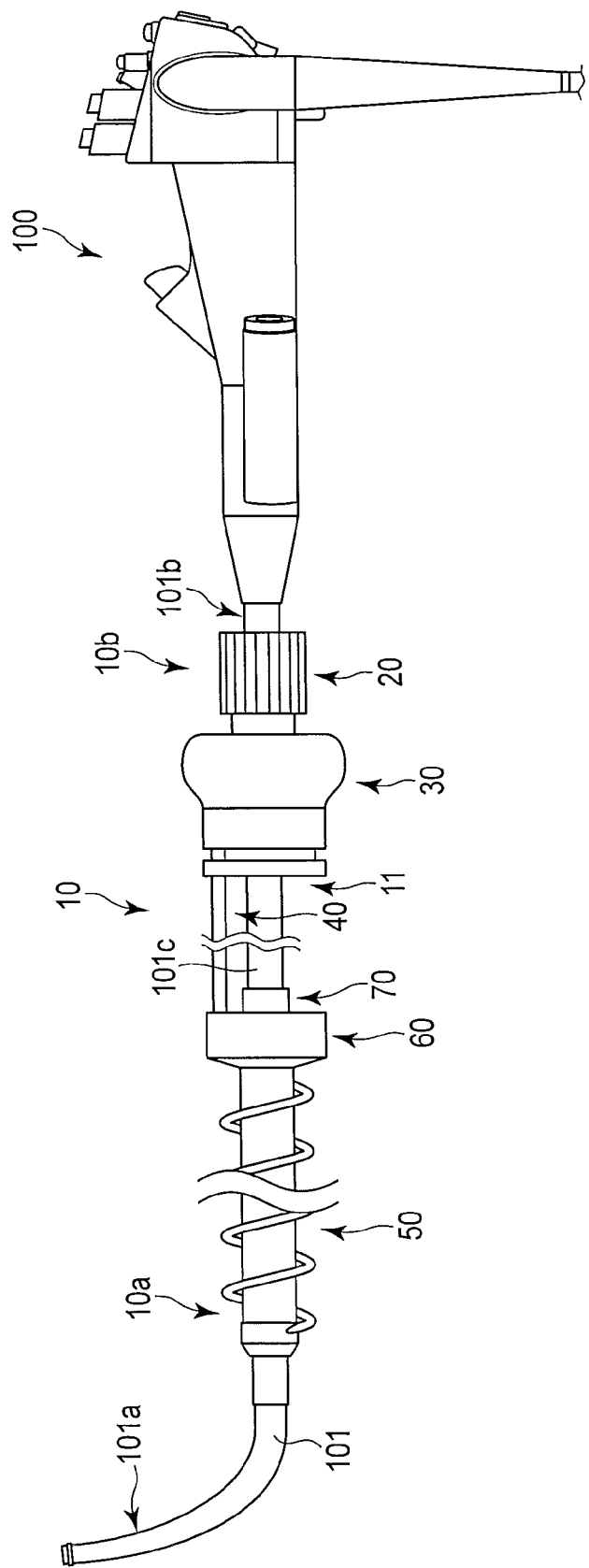
- FIG. 1 is a schematic view of an endoscope that a biological introduction apparatus according to a first embodiment of the present invention is attached.

As shown in FIG. 1, the endoscope 100 has an insertion unit 101 having the longitudinal axis. This insertion unit 101 has a distal end portion 101a, a proximal end portion 101b, and an intermediate portion 101c arranged between the distal end portion 101a and the proximal end portion 101b. The endoscope 100 has a later-described biological introduction apparatus 10. It is to be noted that the endoscope 100 may be integrated with or separated from the biological introduction apparatus 10.

[Outline of Biological Introduction Apparatus 10]

The biological introduction apparatus 10 shown in FIG. 1 and FIG. 2 is introduced into a living body when the endoscope 100 observes, for example, an observation target arranged in the living body. At this time, the biological introduction apparatus 10 is introduced into the living body in a state that the insertion unit 101 of the endoscope 100 is being inserted through the biological introduction apparatus 10. The inside the living body means a lumen such as the inside of a small intestine, the inside of a large intestine, a pylorus, a duodenum, a cardia, and others. The observation target means, for example, an affected part or a lesioned part in a lumen.

Furthermore, the biological introduction apparatus 10 is also an auxiliary apparatus that aids insertion and removal of the insertion unit 101 when the insertion unit 101 of the endoscope 100 is inserted into or removed from (forward or backward movement), for example, a living body.

[Configuration of Biological Introduction Apparatus 10]

As shown in FIG. 1 and FIG. 2, the biological introduction apparatus 10 has a distal end portion 10a and a proximal end portion 10b. Moreover, as shown in FIG. 1 and FIG. 2, the biological introduction apparatus 10 has a proximal end portion side positioning mechanism 20, a drive force generation and input mechanism 30, a drive force transmission mechanism 40, a distal end portion side positioning mechanism 70, a holding member 60, and a helical rotation member 50 from the proximal end portion 10b side of the biological introduction apparatus 10 toward the distal end portion 10a side of the biological introduction apparatus 10.

The proximal end portion side positioning mechanism 20, the drive force generation and input mechanism 30, the distal end portion side positioning mechanism 70, the holding member 60, and the helical rotation member 50 are arranged on, for example, the same axis so that the insertion unit 101 is arranged in the proximal end portion side positioning mechanism 20, the drive force generation and input mechanism 30, the distal end portion side positioning mechanism 70, the holding member 60, and the helical rotation member 50 along the longitudinal axis direction.

[Proximal End Portion Side Positioning Mechanism 20]

As shown in FIG. 1, the proximal end portion side positioning mechanism 20 is arranged on the outermost proximal end portion 10b of the biological introduction apparatus 10. This proximal end portion side positioning mechanism 20 positions the proximal end portion 10b side of the biological introduction apparatus 10 to the proximal end portion 101b of the insertion unit 101. In other words, for example, the proximal end portion side positioning mechanism 20 enables the proximal end portion 10b side of the biological introduction apparatus 10 to be attached to the proximal end portion 101b of the insertion unit 101 and positions the proximal end portion 10b side of the biological introduction apparatus 10 to the proximal end portion 101b of the insertion unit 101. In this manner, the proximal end portion side positioning mechanism 20 is an attaching and fixing mechanism that attaches and fixes the biological introduction apparatus 10 to the insertion unit 101. As shown in FIG. 1 and FIG. 2, the proximal end portion side positioning mechanism 20 is coupled with the drive force generation and input mechanism 30.

Figure 3A:
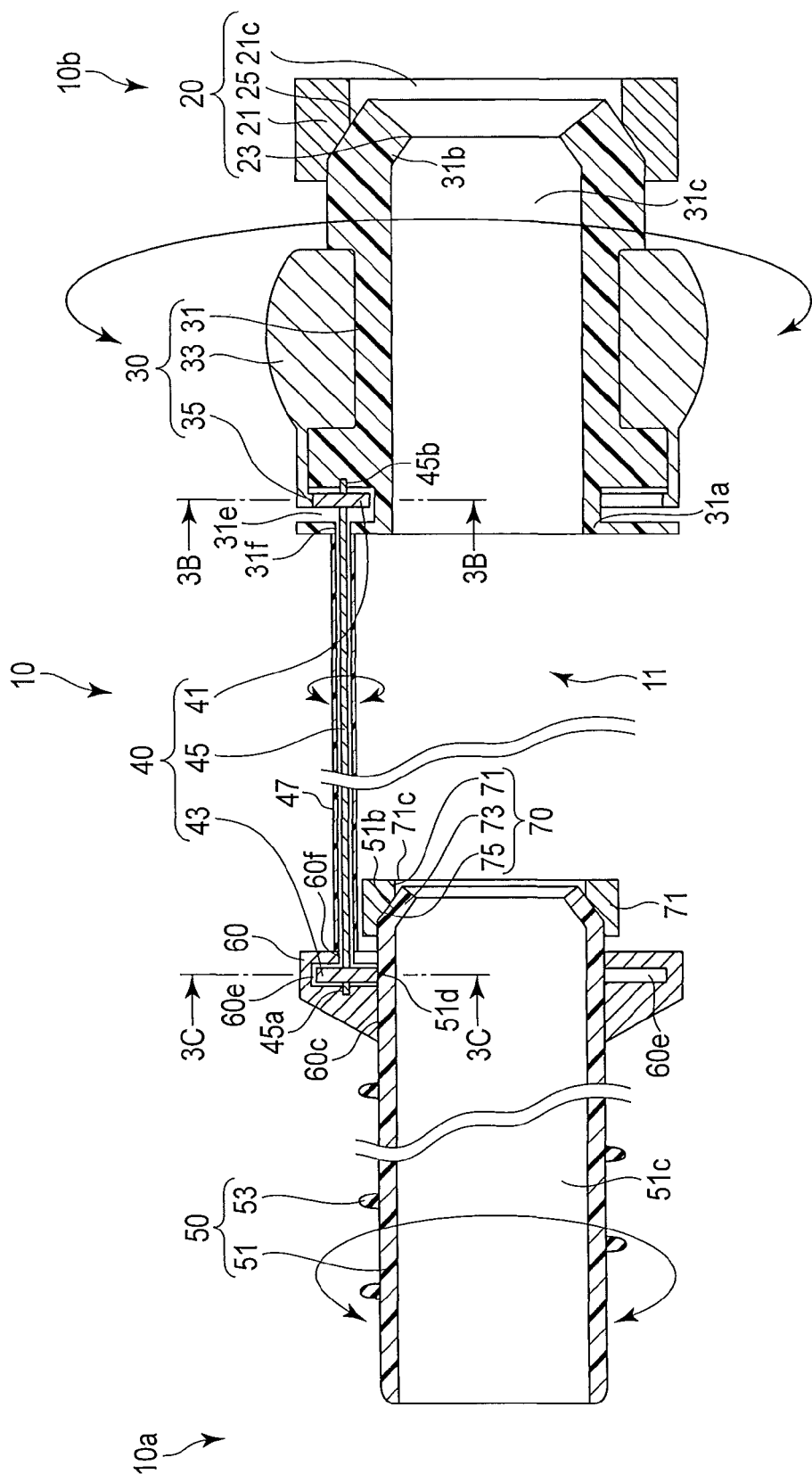
FIG. 3A is a cross-sectional view of the biological introduction apparatus shown in FIG. 2.

As shown in FIG. 2 and FIG. 3A, the proximal end portion side positioning mechanism 20 has a cylindrical main body portion 21 having an insertion hole 21c through which the insertion unit 101 is inserted.

Figure 3B:
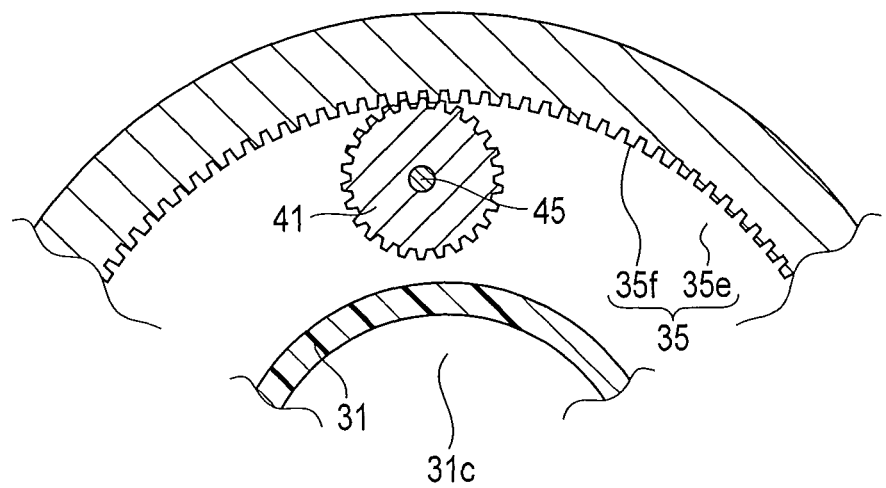
FIG. 3B is a schematic cross-sectional view taken along line 3B-3B shown in FIG. 3A.
Figure 3C:
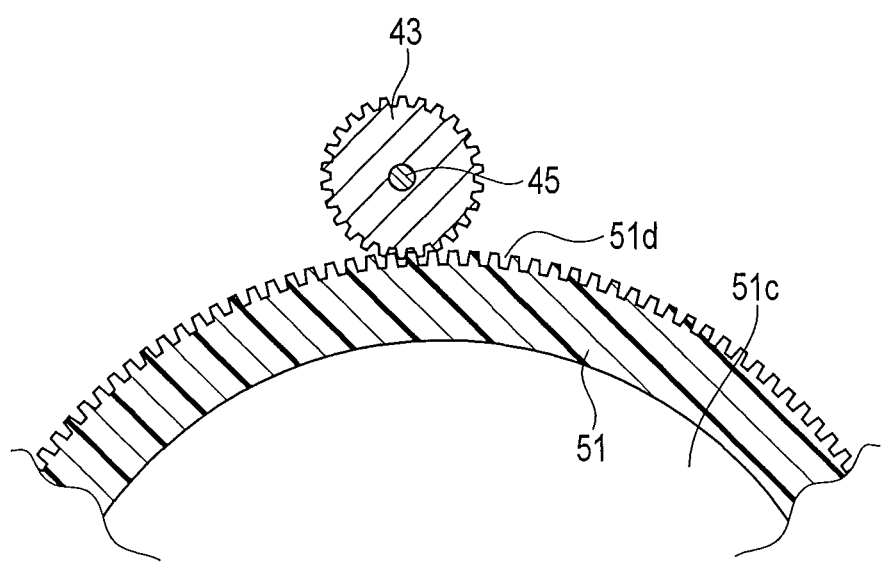
FIG. 3C is a schematic cross-sectional view taken along line 3C-3C shown in FIG. 3A.
Figure 3D:
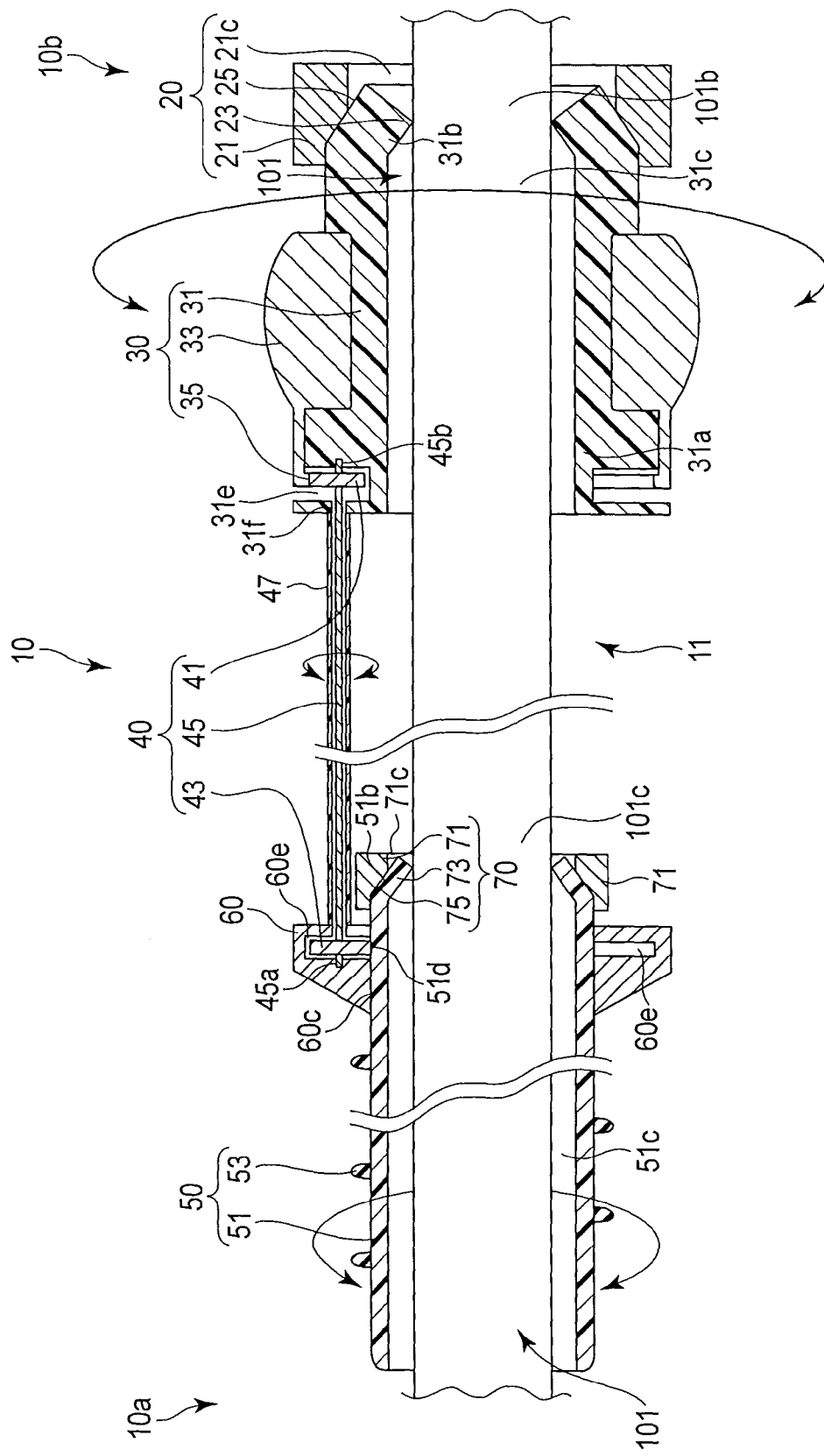
FIG. 3D is a cross-sectional view showing a state that the biological introduction apparatus depicted in FIG. 3A is positioned in an insertion unit of the endoscope.

Additionally, as shown in FIG. 3A and FIG. 3D, the proximal end portion side positioning mechanism 20 has an abutting portion 23 that abuts on an outer peripheral surface of the insertion unit 101 that is inserted through a proximal end portion 31b of a later-described main body portion 31 to position the proximal end portion 10b side of the biological introduction apparatus 10 to the insertion unit 101. The abutting portion 23 is formed at the proximal end portion 31b of the later-described main body portion 31 of the drive force generation and input mechanism 30 through which the insertion unit 101 is inserted, and it is inserted into the insertion hole 21c.

Further, as shown in FIG. 3D and FIG. 3D, the proximal end portion side positioning mechanism 20 has a diameter reducing portion 25 that is arranged in insertion hole 21c, reduces the diameter of the proximal end portion 31b of the main body portion 31 so that the abutting portion 23 abuts on the outer peripheral surface of the insertion unit 101.

As shown in FIG. 3A, the main body portion 21 is a grip portion of the biological introduction apparatus 10 gripped by, for example, an operator. The main body portion 21 is screwed on an outer peripheral surface of the main body portion 31 when the proximal end portion 31b of the main body portion 31 is inserted into the insertion hole 21c.

As shown in FIG. 3A, the insertion hole 21c is formed of the frustum-shaped diameter reducing portion 25 whose diameter is reduced from the distal end portion 10a side of the biological introduction apparatus 10 toward the proximal end portion 10b side of the same and a cylindrical portion which communicates with the diameter reducing portion 25 along the longitudinal axis direction, is arranged on the proximal end portion 10b side than the diameter reducing portion 25, and has a cylindrical shape.

As shown in FIG. 3D, in the diameter reducing portion 25, a maximum diameter of the diameter reducing portion 25 is larger than an external diameter of the insertion unit 101 and substantially equal to an external diameter of the main body portion 31. Additionally, a minimum diameter of the diameter reducing portion 25 is larger than the external diameter of the insertion unit 101 and equal to the diameter of the cylindrical portion.

As shown in FIG. 3A, the abutting portion 23 corresponds to, for example, an edge portion of the proximal end portion 31b and has a ring-like shape. The abutting portion 23 covers the outer peripheral surface of the insertion unit 101. Further, as shown in FIG. 3D, when the proximal end portion 31b of the main body portion 31 is inserted into the insertion hole 21c and bends to reduce its diameter by the diameter reducing portion 25, the abutting portion 23 abuts on the outer peripheral surface of the insertion unit 101.

The abutting portion 23 may have an adhesion member such as a resin O-ring that adheres tightly to the outer peripheral surface of the insertion unit 101.

As shown in FIG. 3A and FIG. 3D, when the proximal end portion 31b of the main body portion 31 is inserted into the insertion hole 21c, the diameter reducing portion 25 bends the proximal end portion 31b of the main body portion 31 and reduces its diameter so that the abutting portion 23 abuts on the outer peripheral surface of the insertion unit 101.

[Drive Force Generation and Input Mechanism 30]

As shown in FIG. 2 and FIG. 3A, the drive force generation and input mechanism 30 generates drive force by rotating in a periaxial direction of the longitudinal axis and inputs this drive force to the drive force transmission mechanism 40. As shown in FIG. 3A, the drive force generation and input mechanism 30 is arranged on the distal end portion 10a side of the main body portion 21. As shown in FIG. 3A, the drive force generation and input mechanism 30 has an insertion hole 31c through which the insertion unit 101 is inserted. As shown in FIG. 1, the drive force generation and input mechanism 30 is installed on the proximal end portion 101b side of the insertion unit 101.

As shown in FIG. 2 and FIG. 3A, the drive force generation and input mechanism 30 has a cylindrical main body portion 31 which is inserted into the insertion hole 21c and coupled with the main body portion 21 and through which the insertion unit 101 is inserted, a drive force generating portion (which will be referred to as a generating portion 33) which is arranged on an outer peripheral surface of the main body portion 31 to be rotatable around the longitudinal axis and generates drive force by rotating, and a drive force input portion (which will be referred to as an input portion 35) which is arranged at a distal end portion of the generating portion 33 to be integral with the distal end portion of the generating portion 33 and inputs the drive force generated by the generating portion 33 to the drive force transmission mechanism 40.

The main body portion 31 has flexibility. Furthermore, as shown in FIG. 3A, the main body portion 31 has a distal end portion 31a which is exposed from the main body portion 21 when the main body portion 31 is coupled with the main body portion 21, a proximal end portion 31b which is inserted into the insertion hole 21c and whose diameter is reduced by the diameter reducing portion 25, and an insertion hole 31c which is arranged on the central axis of the main body portion 31 and through which the insertion unit 101 can be inserted.

As shown in FIG. 3A, the distal end portion 31a has a groove portion 31e which is separated from insertion hole 31c and arranged on the outer side than the insertion hole 31c in the radial direction of the main body portion 31. The groove portion 31e is arranged so that the input portion 35 is arranged in the groove portion 31e, and the input portion 35 meshes with a later-described gear 41 of the drive force transmission mechanism 40 in the groove portion 31e. Furthermore, the groove portion 31e is arranged so that the input portion 35 rotates together with the generating portion 33 in the groove portion 31e when the generating portion 33 rotates and so that a later-described shaft member 45 of the drive force transmission mechanism 40 rotates in the groove portion 31e through the gear 41 by this rotation. Therefore, for example, the groove portion 31e is concaved from the outer peripheral surface toward the inner peripheral surface of the main body portion 31, and it is arranged on the outer peripheral surface of the main body portion 31 over the entire circumference of the main body portion 31 along the periaxial direction of the main body portion 31.

Moreover, as shown in FIG. 3A, the distal end portion 31a has a through hole 31f that is arranged along the longitudinal axis direction and is pierced in an edge portion of the distal end portion 31a to communicate with the groove portion 31e and the outside in the longitudinal axis direction. The through hole 31f is separated from the insertion hole 31c, and it is arranged on the outer side than the insertion hole 31c along the radial direction of the main body portion 31. A proximal end portion 45b of the shaft member 45 is inserted into the through hole 31f so that the gear 41 can be arranged in the groove portion 31e.

As shown in FIG. 3A and FIG. 3D, the proximal end portion 31b has the abutting portion 23 that functions as an edge portion of the proximal end portion 31b. Since the main body portion 31 has flexibility, the diameter of the proximal end portion 31b can be reduced by the diameter reducing portion 25 to provide a tapered shape when the proximal end portion 31b is inserted into the insertion hole 21c. At this time, the abutting portion 23 can abut on the outer peripheral surface of the insertion unit 101. When the proximal end portion 31b is inserted into the insertion hole 21c, the main body portion 31 is screwed to the main body portion 21.

As shown in FIG. 3A, when the main body portion 31 is coupled with the main body portion 21, the insertion hole 31c is arranged coaxially with the insertion hole 21c, and it communicates with the insertion hole 21c.

As shown in FIG. 3A, the generating portion 33 can rotate around the longitudinal axis direction with respect to the main body portion 31. The generating portion 33 has, for example, a ring-like shape. The generating portion 33 is arranged on the outer side than the insertion hole 31c and the main body portion 31 in the radial direction. Additionally, the generating portion 33 is exposed from the main body portion 21 in the axial direction when the main body portion 31 is coupled with the main body portion 21. The generating portion 33 is arranged to be closer to the distal end portion 10a side of the biological introduction apparatus 10 than the main body portion 21, and the generating portion 33 is an operation unit that is operated by fingers of an operator who grips the main body portion 21. Therefore, it is preferable for the generating portion 33 to protrude than the main body portion 21 in the radial direction, for example.

As shown in FIG. 3A, the input portion 35 is bent, for example, from the outer peripheral surface side of the generating portion 33 toward the inner peripheral surface side of the generating portion 33 so that it can be arranged in the groove portion 31e. The input portion 35 is arranged on the outer side than the insertion hole 31c in the radial direction of the main body portion 31.

As shown in FIG. 3B, the input portion 35 has a ring-shaped groove portion 35e which is arranged on a distal end surface of the distal end portion of the generating portion 33 in the longitudinal axis direction and concaved from the distal end portion of the generating portion 33 toward the proximal end portion of the generating portion 33 and an inner peripheral tooth portion 35f that is arranged on the peripheral surface of the groove portion 35e and meshes with the later-described gear 41 of the drive force transmission mechanism 40.

The input portion 35 rotates with the generating portion 33 when the generating portion 33 rotates. As a result, the input portion 35 rotates the shaft member 45 through the gear 41 meshing with the inner peripheral tooth portion 35f. In this manner, the input portion 35 inputs the drive force generated by rotation of the generating portion 33 to the shaft member 45.

[Drive Force Transmission Mechanism 40]

Such a drive force transmission mechanism 40 as shown in FIG. 1 and FIG. 2 transmits the drive force input by the drive force generation and input mechanism 30 to the helical rotation member 50. The drive force transmission mechanism 40 is arranged on the distal end portion 10a side of the biological introduction apparatus 10 than the drive force generation and input mechanism 30. Furthermore, as shown in FIG. 1 and FIG. 3D, in the radial direction of the insertion unit 101, the drive force transmission mechanism 40 is arranged on the outer side than the insertion unit 101 which is inserted through the insertion hole 30c. As shown in FIG. 1 and FIG. 2, the drive force transmission mechanism 40 is arranged along the longitudinal axis direction. Moreover, the drive force transmission mechanism 40 is not arranged over the entire circumference of the biological introduction apparatus 10 in the circumferential direction of the same, but it is arranged on part of the circumference alone and does not cover the insertion unit 101. Therefore, as shown in FIG. 2, the drive force transmission mechanism 40 has, for example, a columnar shape.

As shown in FIG. 3A, FIG. 3B, and FIG. 3C, the drive force transmission mechanism 40 has the gear 41 that meshes with the inner peripheral tooth portion 35f of the input portion 35, a gear 43 that meshes with a later-described outer peripheral tooth portion 51d, and an elongated shaft member 45 that has a proximal end portion 45b at which the gear 41 is arranged and a distal end portion 45a at which the gear 43 is arranged and that is arranged along the longitudinal axis direction.

As shown in FIG. 3A, the gear 41 is arranged at the proximal end portion 45b of the shaft member 45, the gear 43 is arranged at the distal end portion 45a of the shaft member 45, and the shaft member 45 is arranged along the longitudinal axis direction. Moreover, the gear 41 is arranged in the groove portion 31e that is arranged on the outer side than the insertion hole 31c in the radial direction of the main body portion 31. In more detail, as shown in FIG. 3B, the gear 41 is arranged in the groove portion 35e and meshes with the inner peripheral tooth portion 35f. Therefore, the drive force transmission mechanism 40 is arranged to deviate to the outer side than the insertion hole 31c in the radial direction. That is, the drive force transmission mechanism 40 is arranged on the outer side of the insertion unit 101.

As shown in FIG. 1 and FIG. 2, such a drive force transmission mechanism 40 is also a coupling member that couples the proximal end portion 10b side of the biological introduction apparatus 10 including the main body portion 21 and the drive force generation and input mechanism 30 with the distal end portion 10a side of the biological introduction apparatus 10 including the holding member 60 and the helical rotation member 50.

Additionally, as shown in FIG. 1 and FIG. 2, since the shaft member 45 is long, the proximal end portion 10b side of the biological introduction apparatus 10 including the main body portion 21 and the drive force generation and input mechanism 30 and the distal end portion 10a side of the biological introduction apparatus 10 including the holding member 60 and the helical rotation member 50 are arranged to be apart from each other along the longitudinal axis direction.

Further, as shown in FIG. 1, FIG. 2, and FIG. 3A, since the shaft member 45 is long and the drive force transmission mechanism 40 is arranged on the outer side than the insertion unit 101 in the radial direction of the insertion unit 101, a space portion 11 is formed between the holding member 60 and the drive force generation and input mechanism 30 in the longitudinal axis direction. Furthermore, as shown in FIG. 1 and FIG. 3D, the insertion unit 101 is exposed in the space unit 11. The drive force transmission mechanism 40 is arranged on the outer side than the insertion unit 101 in the radial direction of the insertion unit 101 so that the space portion 11 is formed between the holding member 60 and the drive force generation and input mechanism 30 in the longitudinal axis direction and the insertion unit 101 is exposed in the space portion 11.

As shown in FIG. 3B, the gear 41 does not mesh with the entire inner peripheral tooth portion 35f at the same time, but it meshes with part of the inner peripheral tooth portion 35f. The diameter of the gear 41 is smaller than that of the inner peripheral tooth portion 35f.

The gear 43 is arranged on the outer peripheral surface side of the helical rotation member 50. The gear 43 does not mesh with the entire outer peripheral tooth portion 51d to cover the entire outer peripheral tooth portion 51d. As shown in FIG. 3C, the gear 43 rotates while meshing with part of the outer peripheral tooth portion 51d to thereby rotate the helical rotation member 50 through the outer peripheral tooth portion 51d. The diameter of the gear 43 is smaller than that of the outer peripheral tooth portion 51d.

The shaft member 45 has flexibility. The shaft member 45 is, for example, a torque wire. As shown in FIG. 2 and FIG. 3A, when the input portion 35 rotates by rotation of the generating portion 33, the gear 41 that meshes with the inner peripheral tooth portion 35f of the input portion 35 rotates in accordance with this rotation. As a result, the shaft member 45 having the gear 41 rotates in the periaxial direction of the shaft member 45. Moreover, the gear 43 arranged at the distal end portion 45a of the shaft member 45 rotates. When the gear 43 rotates, the helical rotation member 50 rotates. The shaft member 45 receives drive force from the input portion 35 through the gear 41 arranged at the proximal end portion 45b and rotates in the periaxial direction of the shaft member 45 by the received drive force, whereby the drive force is transmitted to the helical rotation member 50 through the gear 43 arranged at the distal end portion 45a.

It is to be noted that the main body portion 31 rotates in the periaxial direction of the longitudinal axis, but the shaft member 45 rotates in the periaxial direction of the shaft member 45 alone. Therefore, as shown in FIG. 3A, the distal end portion 45a of the shaft member 45 is supported by the holding member 60 and the proximal end portion 45b of the shaft member 45 is supported by the main body portion 31 so that the shaft member 45 rotates in the periaxial direction of the shaft member 45. As described above, the holding member 60 and the main body portion 31 prevent the shaft member 45 from rotating together with the main body portion 31 in the periaxial direction of the longitudinal axis.

As shown in FIG. 3A, the shaft member 45 is inserted through a tubular member 47 that covers the shaft member 45 and has flexibility. The tubular member 47 is, for example, a resin tube. The tubular member 47 has hardness that suppresses torsion of the shaft member 45 when the shaft member 45 transmits drive force to the helical rotation member 50. The tubular member 47 protects the shaft member 45 from resistance from the inner wall. A distal end portion of the tubular member 47 adheres to the proximal end surface of the holding member 60, and a proximal end portion of the tubular member 47 adheres to the distal end surface of the main body portion 31. Like the shaft member 45, the tubular member 47 is arranged on the outer side than the insertion unit 101 in the radial direction of the insertion unit 101, and it is arranged on part of the circumference of the biological introduction apparatus 10 in the circumferential direction of the same.

[Helical Rotation Member 50]

As shown in FIG. 1 and FIG. 3A, the helical rotation member 50 is arranged on the outermost distal end portion 10a side of the biological introduction apparatus 10. The helical rotation member 50 is arranged apart from the drive force generation and input mechanism 30 in the longitudinal axis direction.

As shown in FIG. 1, FIG. 2, and FIG. 3A, the helical rotation member 50 has a cylindrical main body portion 51 through which the insertion unit 101 is inserted and which rotates in the periaxial direction of the longitudinal axis by drive force transmitted from the gear 43 of the drive force transmission mechanism 40 and a fin portion 53 which is arranged on the outer peripheral surface of the main body portion 51 and helically arranged in the periaxial direction of the longitudinal axis.

The main body portion 51 is made of, for example, a resin that can be cleaned and sterilized. The main body portion 51 has flexibility. This resin is, for example, polyurethane.

As shown in FIG. 3A and FIG. 3C, the main body portion 51 has a proximal end portion 51b which is inserted through a later-described insertion hole 60c of the holding member 60, an insertion hole 51c through which the insertion unit 101 is inserted, and an outer peripheral tooth portion 51d which is arranged between the proximal end portion 51b and a proximal end portion of the fin portion 53 in the longitudinal axis direction, arranged on the outer peripheral surface of the main body portion 51 over the entire circumference of the main body portion 51, and meshes with the gear 43 when the proximal end portion 51b is inserted through the insertion hole 60c.

As shown in FIG. 3A, the insertion hole 51c is arranged coaxially with the insertion hole 31c when the main body portion 51 is held by the holding member 60. The diameter of the insertion hole 51c is substantially equal to that of the insertion hole 31c.

As shown in FIG. 3A, the outer peripheral tooth portion 51d is arranged on the proximal end portion 51b side of the fin portion 53 in the longitudinal axis direction. The outer peripheral tooth portion 51d is a drive force receiving portion that the helical rotation member 50 receives drive force. In this manner, the helical rotation member 50 receives the drive force on the proximal end portion side of the helical rotation member 50.

As shown in FIG. 3A, the portion where the outer peripheral tooth portion 51d is arranged is held by the holding member 60 so that the outer peripheral tooth portion 51d meshes with the gear 43 and is arranged in the insertion hole 60c. The outer peripheral tooth portion 51d does not allow insertion of the holding member 60 on the proximal end portion 10b side.

As shown in FIG. 3A, the main body portion 51 receives the drive force from the gear 43 through the outer peripheral tooth portion 51d when the gear 43 rotates with the outer peripheral tooth portion 51d meshing with the gear 43. As a result, the main body portion 51 rotates in the periaxial direction of the longitudinal axis by the drive force.

As shown in FIG. 1, FIG. 2, and FIG. 3A, the fin portion 53 is exposed from the holding member 60, and it is arranged on the distal end portion 10a side of the biological introduction apparatus 10 than the holding member 60. That is, the fin portion 53 is not inserted into the insertion hole 60c. The fin portion 53 is made of, for example, rubber that can be cleaned and sterilized. The fin portion 53 is fixed on the outer peripheral surface of the main body portion 51 by bonding, welding, or the like. As shown in FIG. 1, the fin portion 53 is helically arranged in a clockwise direction when the distal end portion is seen from the proximal end portion 51b of the main body portion 51.

When the insertion unit 101 is inserted into a lumen, the fin portion 53 abuts on an inner wall of the lumen. In this state, when the main body portion 51 rotates in the periaxial direction of the longitudinal direction, the fin portion 53 engages with the inner portion of the lumen, and propulsive force acts on the insertion unit 101 in the longitudinal axis direction. As a result, the insertion unit 101 moves forward and backward (insertion and removal) in the lumen. The propulsive force means insertion force that acts on the insertion unit 101 in the inserting direction of the insertion unit 101 and aids insertion of the insertion unit 101 or removal force that acts on the insertion unit 101 in the removal direction of the insertion unit 101 and aids removal of the insertion unit 101.

When the main body unit 51 rotates in the clockwise direction, the insertion force acts on the insertion unit 101, and insertion properties of the insertion unit 101 are improved. Further, when the main body portion 51 rotates in a counterclockwise direction, the removal force acts on the insertion unit 101, and the insertion properties of the insertion unit 101 are improved.

[Holding Member 60]

As shown in FIG. 3A, the holding member 60 has a cylindrical shape. The holding member 60 has the insertion hole 60c through which the proximal end portion 51b of the main body portion 51 is inserted. As shown in FIG. 1, FIG. 2, and FIG. 3A, the holding member 60 is arranged on the proximal end portion 10b side of the biological introduction apparatus 10 than the fin portion 53. As shown in FIG. 3A, the holding member 60 holds the main body portion 51 in such a manner that the main body portion 51 is coupled with the gear 43 which is the distal end portion of the drive force transmission mechanism 40 through the outer peripheral tooth portion 51d and the main body portion 51 rotates in the periaxial direction of the longitudinal axis by the drive force in a state that the proximal end portion 51b of the main body portion 51 is inserted in the insertion hole 60c. In other words, the holding member 60 holds the helical rotation member 50 in such a manner that the helical rotation member 50 rotates in the periaxial direction of the longitudinal axis by the drive force transmitted by the drive force transmission mechanism 40.

As shown in FIG. 3A, the holding member 60 has the insertion hole 60c into which the main body portion 51 of the helical rotation member 50 is inserted so that the holding member 60 holds the helical rotation member 50 and the helical rotation member 50 rotates in the periaxial direction of the longitudinal axis by the drive force and through which the proximal end portion 51b of the main body portion 51 is inserted toward the proximal end portion 10b side of the biological introduction apparatus 10.

As shown in FIG. 3A, the insertion hole 60c is arranged coaxially with the insertion hole 31c when the holding member 60 is coupled with the main body portion 31 through the drive force transmission mechanism 40. The diameter of the insertion hole 60c is substantially equal to that of the insertion hole 31c.

Moreover, as shown in FIG. 3A, the holding member 60 has a groove portion 60e which is separated from insertion hole 60c, is arranged on the outer side than the insertion hole 60c in the radial direction of the holding member 60 and communicates with the insertion hole 60c in the radial direction of the holding member 60 and a through hole 60f which is arranged along the longitudinal axis direction and pierced in the proximal end portion of the holding member 60 to communicate with the groove portion 60e and the outside in the longitudinal axis direction.

The groove portion 60e is arranged in such a manner that the gear 43 of the drive force transmission mechanism 40 meshes with the outer peripheral tooth portion 51d of the helical rotation member 50, the gear 43 rotates together with the shaft member 45 in the groove portion 60e when the shaft member 45 rotates, and the helical rotation member 50 rotates through the gear 43 and the outer peripheral tooth portion 51d in the insertion hole 60e in accordance with this rotation. Therefore, the groove portion 60e is concaved from the inner peripheral surface toward the outer peripheral surface of the holding member 60.

The through hole 60f is separated from the insertion hole 60c, and it is arranged on the outer side than the insertion hole 60c in the radial direction of the holding member 60. The distal end portion of the shaft member 45 is inserted through the through hole 60f so that the gear 43 is arranged in the groove portion 60e. The through hole 60f is arranged coaxially with through hole 31f so that the drive force transmission mechanism 40 is linearly arranged.

[Distal End Portion Side Positioning Mechanism 70]

As shown in FIG. 1, the distal end portion side positioning mechanism 70 positions the biological introduction apparatus 10, which is the proximal end portion of the helical rotation member 50 in particular, to the intermediate portion 101c of the insertion unit 101. In other words, the distal end portion side positioning mechanism 70 attaches the biological introduction apparatus 10 to the intermediate portion 101c of the insertion unit 101 and positions the biological introduction apparatus 10 to the intermediate portion 101c of the insertion unit 101. As described above, the distal end portion side positioning mechanism 70 is an attaching and fixing mechanism that attaches and fixes the biological introduction apparatus 10 to the insertion unit 101.

As shown in FIG. 1 and FIG. 3A, the distal end portion side positioning mechanism 70 is arranged on the proximal end portion 10b side of the biological introduction apparatus 10 than the fin portion 53. As shown in FIG. 3A, for example, the distal end portion positioning mechanism 70 is arranged in the vicinity of the proximal end portion of the fin portion 53. In more detail, as shown in FIG. 1, FIG. 2, and FIG. 3A, the distal end portion side positioning mechanism 70 is arranged on the proximal end portion 10b side of the biological introduction apparatus 10 than the holding member 60. As shown in FIG. 3A, the distal end portion side positioning mechanism 70 is formed at the proximal end portion 51b of the main body portion 51 which is inserted through the holding member 60. As shown in FIG. 3A, this distal end portion side positioning mechanism 70 is arranged in the vicinity of the outer peripheral tooth portion 51d which is a drive receiving portion and on the proximal end portion 10b side of the biological introduction apparatus 10 than the outer peripheral tooth portion 51d.

As shown in FIG. 3A and FIG. 3D, the distal end portion side positioning mechanism 70 has a cylindrical main body portion 71 having an insertion hole 71c through which the insertion unit 101 is inserted.

Additionally, as shown in FIG. 3A and FIG. 3D, the distal end portion side positioning mechanism 70 has an abutting portion 73 which is formed at the proximal end portion 51b of the main body portion 51 that is inserted into the insertion hole 71c after inserted through the insertion hole 60c and which abuts on the outer peripheral surface of the insertion unit 101 inserted through the proximal end portion 51b of the main body portion 51 to position the biological introduction apparatus 10 with respect to the insertion unit 101.

Further, as shown in FIG. 3A and FIG. 3D, the distal end portion positioning mechanism 70 has a diameter reducing portion 75 which is arranged in the insertion hole 71c and reduces the diameter of the proximal end portion 51b of the main body portion 51 so that the abutting portion 73 abuts on the outer peripheral surface of the insertion unit 101.

As shown in FIG. 3A, the main body portion 71 is arranged on the insertion unit 101 side than the tubular member 47 and the drive force transmission mechanism 40 in, for example, the radial direction. As shown in FIG. 3A, the main body portion 71 is screwed to the outer peripheral surface of the proximal end portion 51b when the proximal end portion 51b of the main body portion 51 is inserted into the insertion hole 51c.

As shown in FIG. 3A, the insertion hole 71c is formed of the diameter reducing portion 75 having a frustum shape whose diameter is reduced from the distal end portion 10a of the biological introduction apparatus 10 toward the proximal end portion 10b of the same and a cylindrical portion having a cylindrical shape which communicates with the diameter reducing portion 75 in the longitudinal axis direction and is arranged on the proximal end portion 10b side than the diameter reducing portion 75, and has a cylindrical shape.

As shown in FIG. 3A, in the diameter reducing portion 75, a maximum diameter of the diameter reducing portion 75 is larger than an external diameter of the insertion unit 101 and substantially equal to an external diameter of the main body portion 51, and a minimum diameter of the diameter reducing portion 75 is larger than the external diameter of the insertion unit 101 and substantially equal to the diameter of the cylindrical portion.

As shown in FIG. 3D, in this embodiment, when the proximal end portion 51b of the main body portion 51 is inserted through the insertion hole 60c of the holding member 60, the inserted proximal end portion 51b abuts on the outer peripheral surface of the insertion unit 101 inserted through the main body portion 51, thereby positioning the insertion unit 101 with respect to the helical rotation member 50. Therefore, the diameter reducing portion 75 reduces the diameter of the proximal end portion 51b of the main body portion 51 so that the proximal end portion 51b of the main body portion 51 abuts on the outer peripheral surface of the insertion unit 101. In more detail, when the proximal end portion 51b of the main body portion 51 is inserted into the insertion hole 71c, the diameter reducing portion 75 bends the proximal end portion 51b of the main body portion 51 and reduces the diameter of the same so that the abutting portion 73 abuts on the outer peripheral surface of the insertion unit 101.

As shown in FIG. 3A, the abutting portion 73 corresponds to, for example, an edge portion of the proximal end portion 51b and has a ring-like shape. The abutting portion 73 covers the outer peripheral surface of the insertion unit 101. Furthermore, as shown in FIG. 3D, when the proximal end portion 51b of the main body portion 51 is inserted into the insertion hole 71c and bends to reduce its diameter by the diameter reducing portion 75, the abutting portion 73 abuts on the outer peripheral surface of the insertion unit 101.

As shown in FIG. 3A, the proximal end portion 51b has the abutting portion 73 that functions as the edge portion of the proximal end portion 51b. Since the main body portion 51 has the flexibility, the diameter of the proximal end portion 51b can be reduced by the diameter reducing portion 75 to provide a tapered shape when the proximal end portion 51b is inserted into the insertion hole 71c. At this time, the abutting portion 73 can abut on the outer peripheral surface of the insertion unit 101. When the proximal end portion 51b is inserted in the insertion hole 71c, the main body portion 71 is screwed to the main body portion 51.

The abutting portion 73 may have an adhesion member such as a rein O-ring that adheres tightly to the outer peripheral surface of the insertion unit 101.

In this manner, the distal end portion of the helical rotation member 50 is a free end, and the proximal end portion of the helical rotation member 50 is a fixed end. This fixed end is positioned to the intermediate portion 101c of the insertion unit 101, and it is close to the drive force receiving portion of the helical rotation member 50.

[Example of Attachment and Positioning]

The drive force generation and input mechanism 30 is coupled with the drive force transmission mechanism 40 so that the gear 41 meshes with the inner peripheral tooth portion 35f. At this time, the main body portion 31 is not attached to the main body portion 21.

Then, the helical rotation member 50 is coupled with the drive force transmission mechanism 40 and held by the holding member 60 so that the proximal end portion 51b of the main body portion 51 is inserted through the insertion hole 60c of the holding member 60 and the outer peripheral tooth portion 51d meshes with the gear 43 at the time of insertion. At this time, the main body portion 51 is not attached to the main body portion 71.

As a result, the proximal end portion 10b side of the biological introduction apparatus 10 including the drive force generation and input mechanism 30 side is coupled with the distal end portion 10a side of the biological introduction apparatus 10 including the holding member 60 and the helical rotation member 50 by the drive force transmission mechanism 40. At this time, the insertion hole 31c and the insertion hole 51c are arranged on the same straight line. Further, the drive force transmission mechanism 40 is arranged on the outer side than the insertion hole 31c in the radial direction. Furthermore, the space portion 11 is formed between the holding member 60 and the drive force generation and input mechanism 30 in the longitudinal axis direction.

Then, the main body portion 21 is arranged on the proximal end portion 10b side of the biological introduction apparatus 10 than the main body portion 31 so that the insertion hole 21c and the insertion hole 31c are arranged on the same straight line each other. Moreover, the main body portion 71 is arranged in the space portion 11 in such a manner that the insertion hole 51c and the insertion hole 71c are arranged on the same straight line each other and also arranged on the insertion unit 101 side than the tubular member 47 and the drive force transmission mechanism 40 in the radial direction.

Then, the insertion unit 101 is inserted through the insertion holes 51c, 71c, 31c, and 21c so that the proximal end portion 101b side of the insertion unit 101 is arranged on the main body portion 21 side and the distal end portion 101a side of the insertion unit 101 is arranged on the helical rotation member 50 side.

Subsequently, the main body portion 21 is screwed on the outer peripheral surface of the proximal end portion 31b of the main body portion 31 so that the diameter of the proximal end portion 31b is reduced by the diameter reducing portion 25 and the abutting portion 23 abuts on the outer peripheral surface of the proximal end portion 101b of the insertion unit 101. At this time, since the abutting portion 23 abuts on the outer peripheral surface of the proximal end portion 101b of the insertion unit 101, the biological introduction apparatus 10 is positioned with respect to the proximal end portion 101b of the insertion unit 101.

Then, the main body portion 71 is screwed with respect to the outer peripheral surface of the proximal end portion 51b of the main body portion 51 so that the diameter of the proximal end portion 51b is reduced by the diameter reducing portion 75 and the abutting portion 73 abuts on the outer peripheral surface of the intermediate portion 101c of the insertion unit 101. At this time, since the abutting portion 73 abuts on the outer peripheral surface of the intermediate portion 101c of the insertion unit 101, the biological introduction apparatus 10 is positioned with respect to the intermediate portion 101c of the insertion unit 101.

As a result, the biological introduction apparatus 10 is attached to the insertion unit 101 while being positioned with respect to the insertion unit 101.

[Function 1]

As described above, in the biological introduction apparatus 10 attached to the insertion unit 101, the main body portion 21 is gripped, and the distal end portion 101a of the insertion unit 101 and the helical rotation member 50 are introduced into a living body. At this time, the fin portion 53 engages with the inner wall of the lumen.

The generating portion 33 is operated by fingers, and it rotates in the periaxial direction of the longitudinal axis. At the same time, the input portion 35 rotates in the periaxial direction of the longitudinal axis together with the generating portion 33 when the generating portion 33 rotates. As a result, the gear 41 meshing with the inner peripheral tooth portion 35f rotates, and the shaft member 45 rotates in the periaxial direction of the shaft member 45.

In this manner, the input portion 35 rotates the shaft member 45 through the gear 41 meshing with the inner peripheral tooth portion 35f. Further, the input portion 35 inputs drive force generated by rotation of the generating portion 33 to the shaft member 45.

When the shaft member 45 rotates, the gear 43 rotates together with the shaft member 45, and the main body portion 51 having the outer peripheral tooth portion 51d meshing with the gear 43 rotates in the periaxial direction of the longitudinal axis.

In this manner, the shaft member 45 receives the drive force from the input portion 35 through the gear 41 and rotates in the periaxial direction of the shaft member 45 by the received drive force. When the shaft member 45 rotates, it transmits the drive force to the helical rotation member 50 through the gear 43, thereby rotating the helical rotation member 50.

Furthermore, the fin portion 53 engages with the inner wall of the lumen, and propulsive force acts on, for example, the helical rotation member 50 in the inserting direction of the insertion unit 101. As a result, insertion of the helical rotation member 50 is aided by the propulsive force.

[Function 2]

In this embodiment, the drive force transmission mechanism 40 is arranged on the outer side than the insertion unit 101 in the radial direction of the insertion unit 101. The drive force transmission mechanism 40 is not arranged on the entire circumference of the biological introduction apparatus 10 in the circumferential direction of the same but it is arranged on part of the circumference of the same. Therefore, when the biological introduction apparatus 10 is inserted into a lumen, the drive force transmission mechanism 40 is hard to receive resistance from the inner wall, thereby suppressing torsion.

As a result, the drive force transmission mechanism 40 assuredly transmits drive force to the helical rotation member 50. Moreover, the helical rotation member 50 assuredly rotates, and the fin portion 53 securely engages with the inner wall. Therefore, a reduction in propulsive force is avoided. In this manner, even if the drive force transmission mechanism 40 receives the resistance, the propulsive force can be prevented from lowering.

Additionally, the tubular member 47 protects the shaft member 45 from the resistance. Therefore, the drive force transmission mechanism 40 assuredly transmits the drive force to the helical rotation member 50.

Further, since the shaft member 45 has flexibility, it assuredly transmits the drive force to the helical rotation member 50 even if it is distorted or receives the resistance.

[Function 3]

In this embodiment, the helical rotation member 50 receives the drive force on the proximal end portion side of the helical rotation member 50 by the outer peripheral tooth portion 51d which is the drive force receiving portion.

Moreover, in this embodiment, the distal end side positioning mechanism 70 is arranged on the proximal end portion 10b side than the fin portion 53 and also arranged at the proximal end portion 51b of the main body portion 51. As a result, the proximal end portion 51b of the main body portion 51 representing the proximal end portion of the helical rotation member 50 is positioned with respect to the intermediate portion 101c of the insertion unit 101 by the distal end side positioning mechanism 70.

At this time, the distal end portion side positioning mechanism 70 is arranged on the proximal end portion 10b side of the biological introduction apparatus 10 than the fin portion 53 in the longitudinal axis direction. In more detail, the distal end portion side positioning mechanism 70 is arranged in the vicinity of the outer peripheral tooth portion 51d which is the drive force receiving portion and on the proximal end portion 10b side of the biological introduction apparatus 10 than the outer peripheral tooth portion 51d.

As described above, in this embodiment, an arrangement position of the drive force receiving portion of the helical rotation member 50 is close to a setting-out position of the main body portion 51. Additionally, the main body portion 51 has flexibility.

In this embodiment, for example, when the biological introduction apparatus 10 is inserted into a lumen and the fin portion 53 receives resistance from an inner wall, the fin portion 53 buckles. Further, the main body portion 51 of the helical rotation member 50 receives resistance through the fin portion 53. This resistance force attempts compressing the main body portion 51 so that a length of the main body portion 51 is shorter than a natural length of the same. Therefore, an interval of respective parts of the fin portion 53 becomes small, the fin portion 53 is hard to engage with the inner wall, and the propulsive force may be possibly lowered.

However, in this embodiment, the proximal end portion 51b of the main body portion 51 is positioned with respect to the intermediate portion 101c of the insertion unit 101, and the main body portion 51 has flexibility. Therefore, the main body portion 51 expands toward the distal end portion 10a by reaction force in proportion as the main body portion 51 receives the resistance force. As a result, the interval between the respective parts of the fin portion 53 can be prevented from narrowing, and the fin portion 53 assuredly engages with the inner wall. As a result, a reduction in propulsive force is avoided.

Moreover, in this embodiment, since the arrangement position of the drive force receiving portion (the outer peripheral tooth portion 51d) of the helical rotation member 50 is close to the setting-out position of the main body portion 51, the reaction force increases when the main body portion 51 receives the resistance, and the main body portion 51 further expands. Therefore, the interval between the respective parts of the fin portion 53 can be prevented from narrowing, and the fin portion 53 assuredly engages with the inner wall. As a result, a reduction in propulsive force can be avoided.

Here, as different from this embodiment, a situation where the main body portion 51 is not positioned will now be described. In this case, when the main body portion 51 receives the resistance, the main body portion 51 allows the insertion unit 101 to slide toward the proximal end portion 10b. Therefore, the insertion unit 101 alone is inserted, the biological introduction apparatus 10 is not introduced, and the propulsive force is lowered. However, this embodiment avoids such a state based on the above description.

Further, as different from this embodiment, a situation where the main body portion 51 is positioned on the distal end portion 10a side will now be described. In this case, likewise, the main body portion 51 receives the resistance through the fin portion 53. This resistance force attempts expanding the main body portion 51 so that a length of the main body portion 51 is longer than a natural length of the same. However, since the main body portion 51 has flexibility, the main body portion 51 compresses toward the distal end portion 10a by reaction force in proportion as the main body portion 51 receives the resistance force. As a result, an interval between respective parts of the fin portion 53 narrows, and the fin portion 53 is hard to engage with an inner wall. As a result, a reduction in propulsive force may possibly occur. However, this embodiment avoids such a state based on the above description.

[Effect]

In this embodiment, the drive force transmission mechanism 40 is arranged on the outer side than the insertion unit 101 in the radial direction of the insertion unit 101. The drive force transmission mechanism 40 is not arranged on the entire circumference of the biological introduction apparatus 10 in the circumferential direction thereof, but it is arranged on part of the circumference alone. Therefore, in this embodiment, the drive force transmission mechanism 40 hardly receives resistance from an inner wall, thereby suppressing torsion of the drive force transmission mechanism 40. Therefore, in this embodiment, the drive force can be assuredly transmitted to the helical rotation member 50, the helical rotation member 50 can be assuredly rotated, and the fin portion 53 can assuredly engage with the inner wall, thus avoiding a reduction in propulsive force.

Moreover, in this embodiment, the tubular member 47 covers the shaft member 45 and protects the shaft member 45 against the resistance. As a result, in this embodiment, the shaft member 45 can be prevented from being distorted by the resistance, and the drive force can be assuredly transmitted to the helical rotation member 50.

Additionally, in this embodiment, the distal end portion side positioning mechanism 70 is arranged on the proximal end portion 10b side than the fin portion 53 and is also arranged at the proximal end portion 51b of the main body portion 51. Further, the arrangement position of the drive force receiving portion (the outer peripheral tooth portion 51d) of the helical rotation member 50 is close to the setting-out position of the main body portion 51. Further, the main body portion 51 has flexibility. As a result, in this embodiment, an interval between respective parts of the fin portion 53 can be prevented from narrowing, the fin portion 53 can assuredly engage with an inner wall, and a reduction in propulsive force can be avoided.

Furthermore, in this embodiment, the abutting portion 73 can be easily allowed to abut on the outer peripheral surface of the insertion unit 101 by using the diameter reducing portion 75, and the insertion unit 101 can be easily positioned.

Moreover, in this embodiment, the insertion unit 101 is inserted through the biological introduction apparatus 10, and then the abutting portion 73 abuts on the outer peripheral surface of the insertion unit 101. Therefore, when the insertion unit 101 is inserted through the biological introduction apparatus 10, the outer peripheral surface of the insertion unit 101 can be prevented from becoming worn away by sliding or the like, thus easily enabling positioning.

Moreover, in this embodiment, for example, the inner peripheral surface of the main body portion 51 does not abut on the outer peripheral surface of the insertion unit 101, but only the ring-shaped abutting portion 73 corresponding to the edge portion of the proximal end portion 51b abuts on the outer peripheral surface of the insertion unit 101. As described above, in this embodiment, the positioning can be easily carried out.

Additionally, in this embodiment, the positioning can be assuredly carried out by using the two positioning mechanisms.

[Modification 1]

Figure 4B:
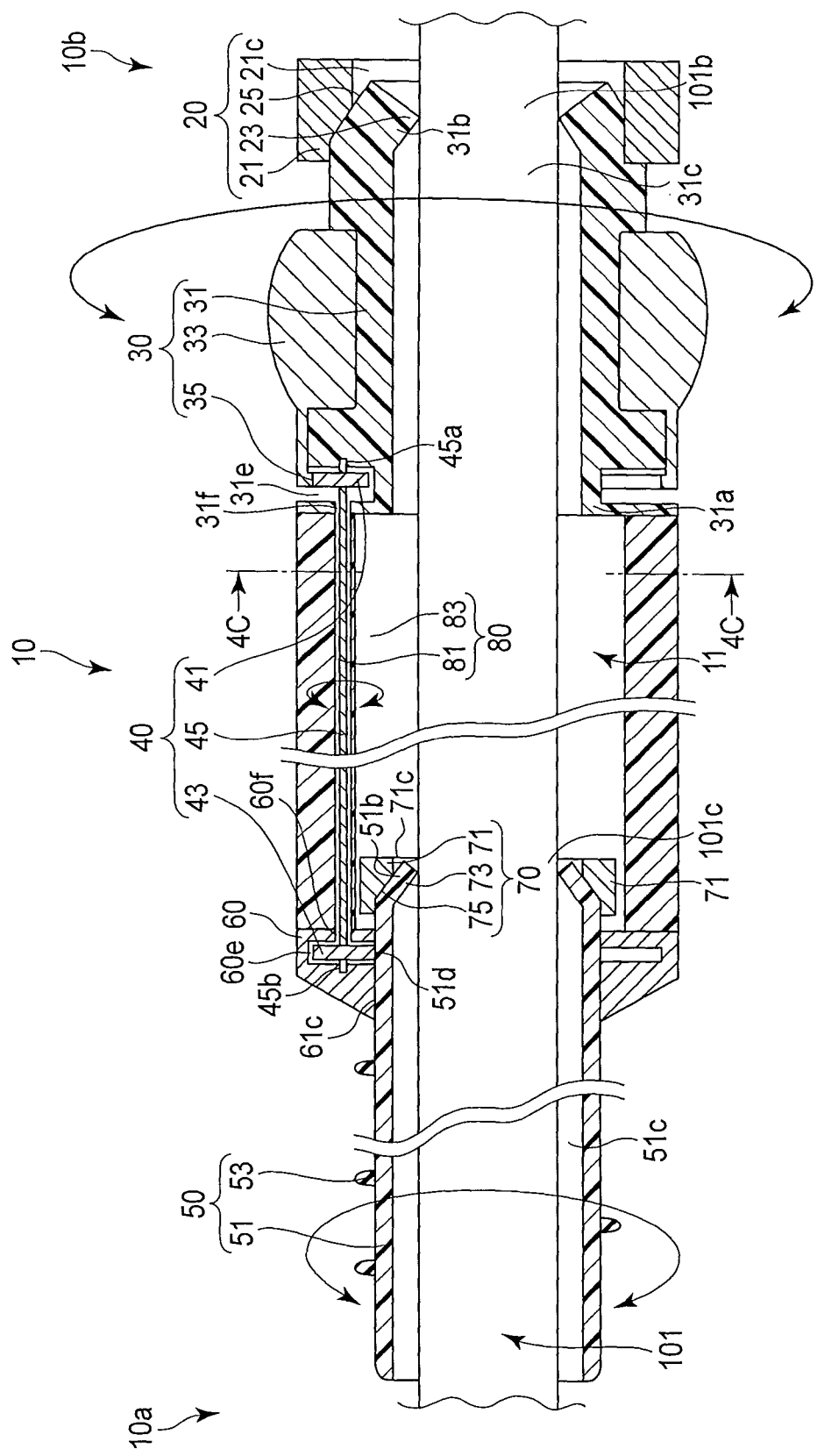
FIG. 4B is a cross-sectional view showing a state that the biological introduction apparatus depicted in FIG. 4A is positioned in an insertion unit of an endoscope.

Although the shaft member 45 is covered with the tubular member 47, it is not restricted thereto. As shown in FIG. 4A, FIG. 4B, and FIG. 4C, the shaft member 45 may be inserted through a channel 81 arranged in a thick wall portion of an over-tube 80. In this case, the over-tube 80 is arranged between the drive force generation and input mechanism 30 and the holing member 60 in the longitudinal axis direction. The channel 81 is arranged along the longitudinal axis direction.

The over-tube 80 has an insertion hole 83 which communicates with the insertion hole 31c and the insertion hole 60c and in which the insertion unit 101 is inserted and the main body portion 71 is arranged.

Further, the over-tube 80 has an opening portion 85 which is arranged in a peripheral surface of the over-tube 80 and is opened toward the outside so that the main body portion 71 is operated. The main body portion 71 is operated through the opening portion 85 so that the diameter of the proximal end portion 51b is reduced by the diameter reducing portion 75 and the abutting portion 73 abuts on the outer peripheral surface of the insertion unit 101.

[Modification 2]

The drive force generation and input mechanism 30 may have a non-illustrated drive source such as a motor which generates the drive force. In this case, the drive force may be coupled with the input portion 35, or it may be directly coupled with the shaft member 45.

The present invention is not restricted to the foregoing embodiment as it is, and constituent elements can be modified and embodied on the implementation stage without departing from the gist thereof. Furthermore, appropriately combining constituent elements disclosed in the foregoing embodiment enables forming various inventions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A biological introduction apparatus which is introduced into a living body in a state that an insertion unit of an endoscope having a longitudinal axis is inserted therethrough, and has a distal end portion and a proximal end portion, comprising:

a drive force generation and input mechanism which has an insertion hole through which the insertion unit is inserted, is arranged on the proximal end portion side, generates drive force by rotating in a periaxial direction of the longitudinal axis, and inputs the drive force;

a drive force transmission mechanism that is distal to the drive force generation and input mechanism, arranged on an outer side of the insertion unit inserted through the insertion hole in a radial direction of the insertion unit, and arranged on part of a circumference of the biological introduction apparatus in a circumferential direction thereof, the drive force transmission mechanism having an elongated shaft member which rotates in the periaxial direction by the drive force input by the drive force generation and input mechanism to transmit the drive force;

a helical rotation member which has a cylindrical main body portion which has flexibility, through which the insertion unit is inserted, and rotates in the periaxial direction of the longitudinal axis by the drive force transmitted by the shaft member; and a fin portion which is arranged on an outer peripheral surface of the main body portion and also helically arranged in the periaxial direction of the longitudinal axis, the helical rotation member being arranged on the distal end portion side and a distal end portion of the helical rotation member being arranged at the distal end of the biological introduction apparatus;

a holding member which has an insertion hole through which a proximal end portion of the main body portion is inserted, is arranged on the proximal end portion side of the biological introduction apparatus and is further proximal on the apparatus than the fin portion in the longitudinal axis direction, and holds the proximal end portion side of the main body portion in such a manner that the proximal end portion side of the main body portion is coupled with a distal end portion of the shaft member with the proximal end portion of the main body portion being inserted through the insertion hole, the drive force is transmitted from the distal end portion of the shaft member to the proximal end portion side of the main body portion, and the main body portion rotates in the periaxial direction of the longitudinal axis by the drive force; and a positioning mechanism which positions the proximal end portion of the main body portion to an intermediate portion arranged between the distal end portion of the insertion unit and the proximal end portion of the insertion unit in such a manner that the helical rotation member is attached to the insertion unit.

2. The biological introduction apparatus according to claim 1,
wherein the positioning mechanism is arranged on the proximal end portion side of the biological introduction apparatus and is further proximal on the apparatus than the fin portion in the longitudinal axis direction.

3. The biological introduction apparatus according to claim 1 or 2,
wherein the positioning mechanism is formed at the proximal end portion of the main body portion.

4. The biological introduction apparatus according to claim 1,
wherein the positioning mechanism is arranged on the proximal end portion side of the biological introduction apparatus and is further proximal on the apparatus than the holding member.

5. The biological introduction apparatus according to claim 1,
further comprising a proximal end portion side positioning mechanism, which is further proximal on the apparatus than the positioning mechanism, that attaches the proximal end portion of the biological introduction apparatus to the proximal end portion of the insertion unit.

6. The biological introduction apparatus according to claim 1,
wherein the positioning mechanism has a diameter reducing portion which reduces the diameter of the proximal end portion of the main body portion in such a manner that the proximal end portion of the main body portion abuts on an outer peripheral surface of the insertion unit in order to position the insertion unit to the helical rotation member by the proximal end portion of the main body portion abuts on the outer peripheral surface of the insertion unit inserted through the main body portion.

7. The biological introduction apparatus according to claim 1,
wherein the drive force generation and input mechanism is installed on the proximal end portion side of the insertion unit.

8. The biological introduction apparatus according to claim 1,
wherein the drive force generation and input mechanism comprises:
a cylindrical main body portion through which the insertion unit is inserted;
a drive force generating portion which is arranged on the outer peripheral surface of the main body portion of the drive force generation and input mechanism to be rotatable in the periaxial direction of the longitudinal axis, and generates the drive force by rotating; and
a drive force input unit which is arranged to be integral with a distal end portion of the drive force generating portion, and inputs the drive force generated by the drive force generating portion to the shaft member.

9. The biological introduction apparatus according to claim 1,
wherein the shaft member further having a proximal end portion and flexibility, receives the drive force by the drive force input portion at the proximal end portion.

10. The biological introduction apparatus according to claim 9,
wherein the shaft member is inserted through a tubular member which covers the shaft member and has flexibility.

11. The biological introduction apparatus according to claim 10,
wherein the tubular member has hardness that suppresses torsion of the shaft member when the shaft member transmits the drive force to the main body portion of the helical rotation member.

12. The biological introduction apparatus according to claim 9, further comprising an over-tube which is arranged between the drive force generation and input mechanism and the holding member in the longitudinal axis direction, into which the shaft member and the insertion unit are inserted in such a manner that the shaft member and the insertion unit are covered, and which has flexibility.

13. The biological introduction apparatus according to claim 12,
wherein the over-tube has a channel into which the shaft member is inserted.

14. An endoscope comprising the biological introduction apparatus according to claim 1.

15. The biological introduction apparatus according to claim 12, wherein the proximal end portion side of the main body portion is coupled with the distal end portion of the shaft member at an outer peripheral surface of the main body portion.

* * * * *